(12) United States Patent
Cohen et al.

(10) Patent No.: US 8,715,590 B2
(45) Date of Patent: May 6, 2014

(54) MULTIPLEXED LATERAL FLOW ASSAY ARRAYS

(75) Inventors: Marc H. Cohen, Silver Spring, MD (US); Kenneth A. Gabriel, Alexandria, VA (US); Lawrence J. Loomis, Columbia, MD (US)

(73) Assignee: Prognosys LLC, Alexandria, VA (US)

( * ) Notice: Subject to any disclaimer, the term of this patent is extended or adjusted under 35 U.S.C. 154(b) by 850 days.

(21) Appl. No.: 12/541,678

(22) Filed: Aug. 14, 2009

(65) Prior Publication Data

US 2010/0041571 A1  Feb. 18, 2010

Related U.S. Application Data

(60) Provisional application No. 61/188,995, filed on Aug. 15, 2008.

(51) Int. Cl.
*G01N 33/48* (2006.01)
*G01N 33/00* (2006.01)
*G01N 33/487* (2006.01)

(52) U.S. Cl.
CPC ...... *G01N 33/0024* (2013.01); *G01N 33/48771* (2013.01); *G01N 33/487* (2013.01)
USPC .......... 422/412; 422/68.1; 422/420; 422/430; 436/169

(58) Field of Classification Search
USPC ............. 422/68.1, 82.05, 119, 402, 403, 412, 422/414, 420, 430; 436/164, 169, 172, 518; 435/4, 7.1; 600/368; 702/19, 22
See application file for complete search history.

(56) References Cited

U.S. PATENT DOCUMENTS

| | | | |
|---|---|---|---|
| 4,673,657 A * | 6/1987 | Christian | 436/501 |
| 5,602,040 A | 2/1997 | May et al. | |
| 5,658,413 A * | 8/1997 | Kaltenbach et al. | 156/272.8 |
| 5,952,173 A * | 9/1999 | Hansmann et al. | 435/6 |
| 5,976,895 A | 11/1999 | Cipkowski | |
| 6,240,790 B1 * | 6/2001 | Swedberg et al. | 73/863.21 |
| 6,770,487 B2 * | 8/2004 | Crosby | 436/518 |
| 6,887,701 B2 * | 5/2005 | Anderson et al. | 435/287.1 |
| 7,223,364 B1 * | 5/2007 | Johnston et al. | 422/68.1 |
| 2009/0020609 A1 | 1/2009 | Cohen et al. | |
| 2010/0311186 A1 * | 12/2010 | Gregory et al. | 436/501 |

* cited by examiner

*Primary Examiner* — Lyle Alexander

(57) ABSTRACT

A diagnostic test device comprising at least one membrane disposed in any of one, two, and three dimensions; at least one test sample fluid input port that receives and transfers at least one test sample fluid and onto the at least one membrane; at least one contiguous fluid flow manifold within the at least one membrane to multiplex or distribute the at least one test sample fluid; at least one contiguous fluid flow channel that operatively connects the at least one membrane to the at least one contiguous fluid flow manifold; at least one analyte assay test zone disposed within the at least one contiguous fluid flow channel; and at least one chemical capturing reagent disposed within the at least one analyte assay test zone, wherein multiple analyte assay test results are simultaneously obtained and in parallel in the diagnostic test device.

16 Claims, 5 Drawing Sheets

MULTIPLEXED LATERAL FLOW ASSAY ARRAYS

CROSS-REFERENCE TO RELATED APPLICATIONS

This application claims the benefit of U.S. Provisional Application Ser. No. 61/188,995, filed on Aug. 15, 2008, the complete disclosure of which, in its entirety, is herein incorporated by reference.

BACKGROUND

1. Technical Field

The embodiments generally relate to the field of in vitro diagnostics, and more particularly to lateral flow assays to detect analytes.

2. Description of the Related Art

Traditional lateral flow assays, such as "strip" or "dip stick" tests are used for a large number of diagnostics applications. The test membranes may include, but are not limited to, glass, glass fiber, silicone, plastic, paper, aluminum foil, or other porous cellulose and rayon compounds that may be hydrophilic or hydrophobic. Specific lines or zones are "striped" onto or applied to the membrane that contain certain chemical capturing reagents or compounds, designed to react and bind with predefined biological markers which may be present in test sample fluids such as, but not limited to, sputum, urine, blood, water, liquefied food samples, concentrated and liquefied air samples and surface swabbed samples.

When one end of a striped assay is dipped into the sample fluid to be tested, the sample fluid is drawn by capillary action along the longitudinal axis of the membrane analyte assay strip. As target proteins, enzymes or bio-markers migrate along a membrane assay strip, they interact with the striped chemical capturing reagents, producing measurable and detectable changes along striped analyte assay test zone sites. The resulting detectable and measurable changes at striped zones can be due, but not limited to, binding with colloidal gold, latex dyed beads, charcoal beads, or magnetic or paramagnetic beads and particles capable of emitting luminescence, fluorescence, auto-fluorescence, phosphorescence, or chemiluminescence indicia. Often, a quality control analyte assay test binding stripe is co-located within the membrane analyte assay test strip, and is designed to react with a test sample fluid to form at least one detectable and measurable band, indicating the validity and the completion of the analyte assay test.

Strip test technology is well known in the art and includes immunodiagnostic, enzymatic, lateral flow immunochromatography, and related chemistries. Analyte assays employing this technology include pregnancy tests, U.S. Pat. No. 5,602,040 issued to May et al., and an apparatus for performing simultaneous single tests on multiple strips for detecting multiple drugs of abuse, U.S. Pat. No. 5,976,895 issued to Cipkowski, the complete disclosures of which, in their entireties, are herein incorporated by reference.

Methods to imbed strip tests, such as those described above, into machine readable barcodes have been described in U.S. Pat. No. 6,770,487 issued to Crosby and U.S. Patent Publication No. 2009/0020609 published to Cohen et al., the complete disclosures of which, in their entireties, are herein incorporated by reference. Rendering the strip test as a barcode enables simultaneous reading and identification of the data associated with the sample itself as well as the test type, validity, date, location, and results. These data can be conveyed directly to authorized individuals or medical personnel and stored in databases for later prognostics, queries, verification, and archival purposes. Imbedding immunodiagnostic tests into barcodes overcomes problems associated with manual entry of test takers, test type, test parameters, and test results. Manual entry is not only costly, but also introduces an opportunity for errors or loss of test data altogether, which, in the case of diagnostic tests, may compromise patients' safety and clinical outcomes, and in the case of food safety testing, may compromise the quality and safety of the food supply and derivative products posing great risk to public health as well as incurring significant economic costs.

SUMMARY

In view of the foregoing, an embodiment herein provides a diagnostic test device comprising at least one membrane disposed in any of one, two, and three dimensions; at least one test sample fluid input port that receives and transfers at least one test sample fluid and onto the at least one membrane; at least one contiguous fluid flow manifold within the at least one membrane to multiplex or distribute the at least one test sample fluid; at least one contiguous fluid flow channel that operatively connects the at least one membrane to the at least one contiguous fluid flow manifold; at least one analyte assay test zone disposed within the at least one contiguous fluid flow channel; and at least one chemical capturing reagent disposed within the at least one analyte assay test zone, wherein multiple analyte assay test results are simultaneously obtained and in parallel in the diagnostic test device.

The at least one chemical capturing reagent may be applied in the at least one analyte assay test zone to configure any of a multiplexed assay and a multiplexed assay array. Additionally, analyte assays may be simultaneously conducted on multiple, independent test sample fluids. Moreover, multiple chemical capture reagent compounds may be used simultaneously to conduct multiple, distinct, independent analyte assays. The diagnostic test device may further comprise at least one quality control zone operatively connected to the at least one analyte assay test zone, wherein at least one chemical capturing control reagent is applied in at least one analyte assay test zone. Also, the diagnostic test device may further comprise at least one sensor imbedded into the at least one contiguous fluid flow channel, wherein an alteration of a state of the at least one sensor indicates information regarding environmental factors affecting a validity of the diagnostic test device.

Furthermore, at least one different chemical capturing reagent may be applied in the at least one analyte assay test zone, and wherein a presence of targeted analytes is indicated, and quantitatively measurable in the at least one analyte assay test zone. The at least one chemical capturing reagent may be applied in different titrations in the at least one analyte assay test zone, and wherein a presence of targeted analytes is indicated, and is quantitatively measurable in the at least one analyte assay test zone. Additionally, at least one analyte assay or multiplexed analyte assay array reduces the necessary volume of the at least one test sample fluid to a minimum. Preferably, the at least one contiguous fluid flow channel increases the speed of delivery of the at least one test sample fluid to the location of the at least one chemical capturing reagent. Also, any of the multiplexed assay and the multiplexed assay array may be imbedded within machine-readable codes comprising a barcode, wherein the machine-readable codes comprise test sample fluid identifying information, test data, test validity, test type, and test parameters, and wherein the multiple analyte assay test results are indicated by alterations of at least one code within the machine-readable codes.

Another embodiment provides a multiplexed analyte assay array comprising at least one membrane disposed in any of one, two, and three dimensions; at least one test sample fluid input port that receives and transfers at least one test sample fluid and onto the at least one membrane; at least one contiguous fluid flow manifold within the at least one membrane to multiplex or distribute the at least one test sample fluid; at least one contiguous fluid flow channel that operatively connects the at least one membrane to the at least one contiguous fluid flow manifold; at least one analyte assay test zone disposed within the at least one contiguous fluid flow channel; at least one quality control zone operatively connected to the at least one analyte assay test zone; and at least one chemical capturing reagent disposed within the at least one analyte assay test zone, wherein multiple analyte assay test results are simultaneously obtained and in parallel in the diagnostic test device.

Furthermore, the at least one chemical capturing reagent may be applied in the at least one analyte assay test zone. The multiplexed analyte assay array may further comprise at least one sensor imbedded into the at least one contiguous fluid flow channel, wherein an alteration of a state of the at least one sensor indicates information regarding environmental factors affecting a validity of the multiplexed analyte assay array. Preferably, the at least one contiguous fluid flow manifold and the at least one contiguous fluid flow channel are formed in any of two and three dimensions by any of masking, writing, filling, imbedding, printing, etching, lithography, striping, mechanically forming, laser forming, electron beam forming, ion beam forming, stencil forming, thermoforming, molding, and extruding. Also, at least one different chemical capturing reagent may be applied in the at least one analyte assay test zone, and wherein a presence of targeted analytes is indicated, and quantitatively measurable in the at least one analyte assay test zone.

Moreover, a single chemical capturing reagent may be applied in different titrations in the at least one analyte assay test zone, wherein at least one targeted analyte binds with the single chemical capturing reagent, and wherein a presence of the at least one targeted analyte is indicated, and is quantitatively measurable in the at least one analyte assay test zone. Furthermore, the at least one analyte assay or multiplexed analyte assay array reduces the necessary volume of the at least one test sample fluid to a minimum. Preferably, the at least one contiguous fluid flow channel conserves test sample fluid volume. Also, the at least one contiguous fluid flow channel preferably increases the speed of delivery of the at least one test sample fluid to the location of the at least one chemical capturing reagent.

Furthermore, the at least one membrane may comprise a hydrophilic membrane separated by at least one hydrophobic membrane. Additionally, the at least one membrane may comprise a hydrophilic membrane sandwiched between at least one hydrophobic membrane. Also, the hydrophilic membrane and the hydrophobic membrane may be interleaved, wherein a plurality of the interleaved membranes are repeatedly stacked to create a three-dimensional multiplexed analyte assay array structure. The multiplexed analyte assay array may further comprise a barcode comprising machine-readable codes comprising the multiplexed analyte assay array imbedded therein, wherein the machine-readable codes comprise test sample fluid identifying information, test data, test validity, test type, and test parameters, and wherein the multiple analyte assay test results are indicated by alterations of at least one code within the machine-readable codes.

Another embodiment provides an apparatus comprising any of at least one multiplexed analyte assay and at least one multiplexed analyte assay array comprising a diagnostic test device, wherein the diagnostic test device comprises at least one membrane disposed in any of one, two, and three dimensions; at least one test sample fluid input port that receives and transfers at least one test sample fluid and onto the at least one membrane; at least one contiguous fluid flow manifold within the at least one membrane to multiplex or distribute the at least one test sample fluid; at least one contiguous fluid flow channel that operatively connects the at least one membrane to the at least one contiguous fluid flow manifold; at least one analyte assay test zone disposed within the at least one contiguous fluid flow channel; and at least one chemical capturing reagent disposed within the at least one analyte assay test zone, wherein multiple analyte assay test results are simultaneously obtained and in parallel in the diagnostic test device. The apparatus may further comprises a barcode structure comprising machine-readable codes comprising the any of at least one multiplexed analyte assay and at least one multiplexed analyte assay array imbedded therein, wherein the machine-readable codes comprise first data regarding the diagnostic test device comprising any of pre-testing data, test types, lot number, identification number, date of manufacture, date of expiration, environmental factors affecting validity of the multiple analyte assay test results, bounds on operational parameters of the diagnostic test device; and second data regarding the analyte assay test results and validity information of the diagnostic test device after the diagnostic test device has been used. The apparatus further comprises means for transmitting the first data and the second data to authorized databases and web portals.

These and other aspects of the embodiments herein will be better appreciated and understood when considered in conjunction with the following description and the accompanying drawings. It should be understood, however, that the following descriptions, while indicating preferred embodiments and numerous specific details thereof, are given by way of illustration and not of limitation. Many changes and modifications may be made within the scope of the embodiments herein without departing from the spirit thereof, and the embodiments herein include all such modifications.

BRIEF DESCRIPTION OF THE DRAWINGS

The embodiments herein will be better understood from the following detailed description with reference to the drawings, in which.

DETAILED DESCRIPTION OF THE EMBODIMENTS

Figure 1A:
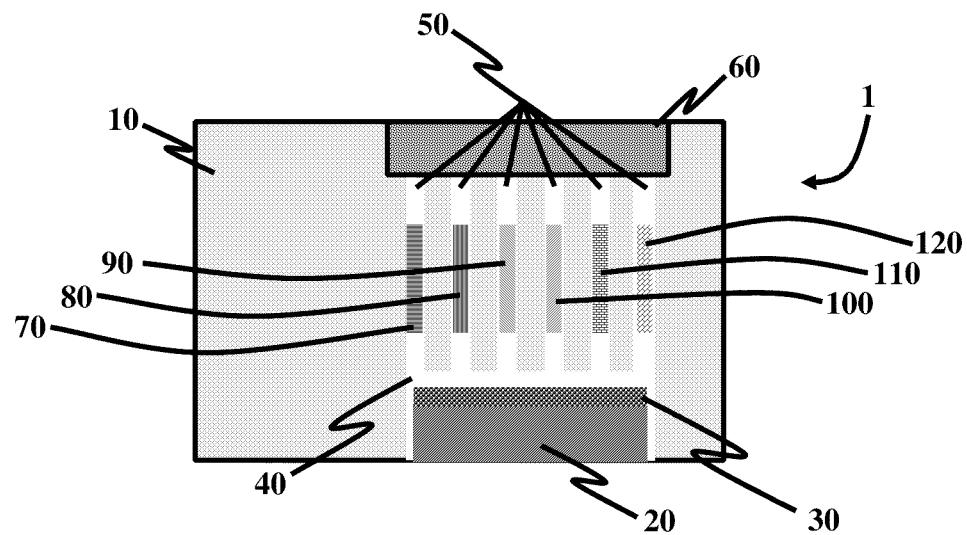
FIG. 1A illustrates a cross-flow, multiplexed analyte assay array wherein the direction of flow of test sample fluid travels across the membrane instead of along the longitudinal axis of the membrane, and wherein one or more chemical capture reagent zones, striped within each fluid flow channel, are designed to give qualitative indicators of the presence or absence of prescribed target analytes in the test sample fluid, according to the embodiments herein.

The embodiments herein and the various features and advantageous details thereof are explained more fully with reference to the non-limiting embodiments that are illustrated in the accompanying drawings and detailed in the following description. Descriptions of well-known components and processing techniques are omitted so as to not unnecessarily obscure the embodiments herein. The examples used herein are intended merely to facilitate an understanding of ways in which the embodiments herein may be practiced and to further enable those of skill in the art to practice the embodiments herein. Accordingly, the examples should not be construed as limiting the scope of the embodiments herein.

The embodiments herein provide lateral flow assays that detect any analyte and create fluid flow channels in any predefined direction within and between the reaction membranes whereby simultaneous, multiple analyte assay testing in multiplexed analyte assays and assay arrays, using one or more test sample fluids is facilitated. These multiplexed analyte assays and assay arrays may be fashioned so that they can be imbedded in one or more machine-readable formats whereby, test data, test parameters and test results, may be conveyed, by information technology systems, to authorized secure databases and web portals.

The embodiments herein enable the use of multiple, and often incompatible, chemistries to detect separate and discrete target analytes from one or more test sample fluids. The embodiments herein makes it possible to detect multiple different bio-markers including, but not limited to antibody, antigen, enzyme and protein, present in the same test sample fluid, because each array constitutes a separate, independent discrete test. By the very nature of the multiplexed, cross-flow analyte assay or assay array structure and function of the embodiments herein, both qualitative and quantitative measures of one or more target analytes can be made. Referring now to the drawings, and more particularly to FIGS. 1A through 5, where similar reference characters denote corresponding features consistently throughout the figures, there are shown preferred embodiments.

The embodiments herein provide a cross-flow analyte assay or cross-flow analyte assay array wherein one or more test sample fluids are introduced through one or more test sample fluid input application ports, and distributed through one or more fluid flow manifolds to one or more fluid flow channels disposed perpendicular or transverse to the longitudinal direction of fluid flow. Each flow channel contains one or more applied chemical capturing reagent zones engineered to react with one or more predetermined target analytes, when present in a test sample fluid.

Specifically, as illustrated in FIG. 1A, a cross-flow multiplexed analyte assay array 1 comprising a membrane analyte assay substrate 10, a test sample fluid input port application pad 20, a marker pad 30 including, but not limited to, colloidal gold, a sample fluid flow manifold 40, multiple multiplexed sample flow channels 50, multiple applied chemical capture reagent zones 70, 80, 90, 100, 110, and 120, and an analyte assay wicking pad 60.

The fluid flow channels 50 created in the membrane substrate 10 support one or more assays or assay arrays which permit the quantitative measurement of the concentration of test sample analytes. By means of calibrated titration of one or more chemical capturing reagents or other sensor chemistry applied to the surface of the membranes used in assays or assay arrays, multiple test zones are created, each with a different concentration of chemical capture reagent or other sensor chemistry. A test sample fluid analyte is multiplexed to each test zone, whereby the quantity of bound target analyte-marker or sensor complex is indicated and rendered measurable.

Figure 1B:
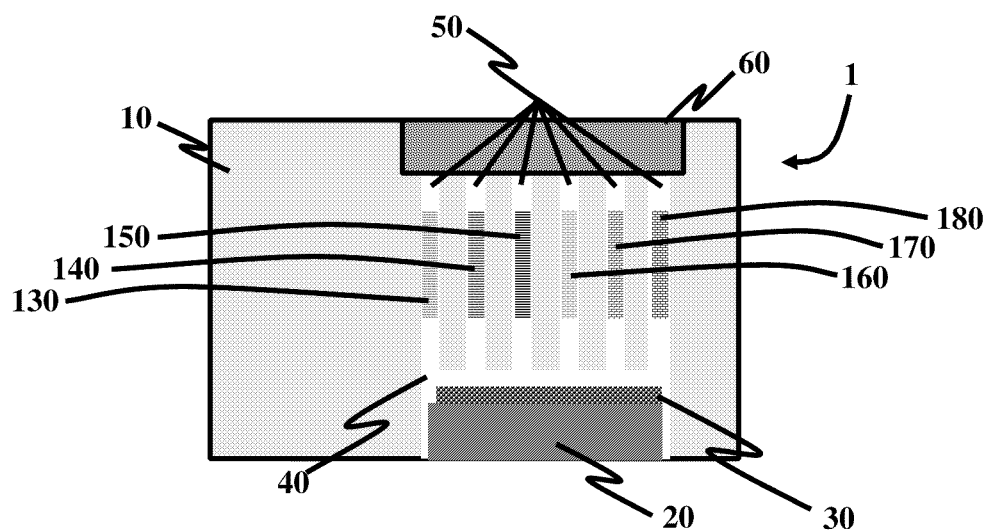
FIG. 1B illustrates a similar cross-flow, multiplexed analyte assay array, as shown in FIG. 1A; however, one or more chemical capture reagent zones striped within each fluid flow channel are designed to give a quantitative indication of the amount of prescribed target analyte, if present in the test sample fluid, according to the embodiments herein.

In FIG. 1B, multiplexed fluid flow channels 50 are shown in an analyte assay array and are striped with different concentrations of the same chemical capturing reagents whereby, each striped chemical capturing reagent zone 130, 140, 150, 160, 170, and 180 indicates quantitative information about the level of a specific targeted test sample fluid analyte, if present in the test sample fluid.

Figure 2:
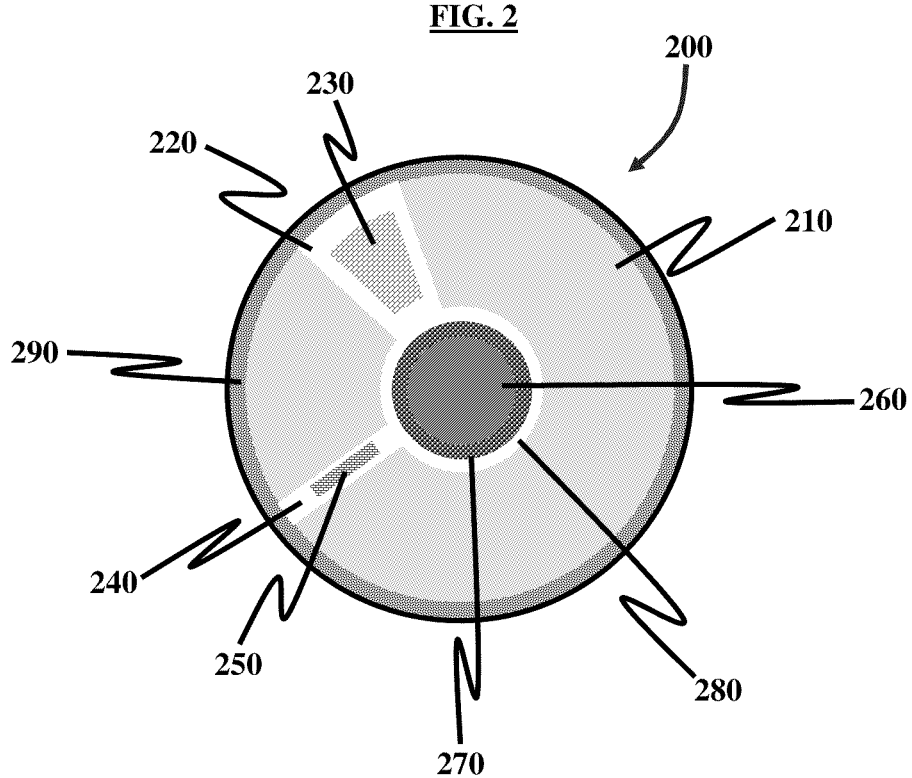
FIG. 2 illustrates a radial-flow and sector-flow multiplexed analyte assay array wherein the test sample fluid is introduced at one or more central ports, and one or more test sample fluids flow in one or more prescribed radial flow channels or in prescribed radial flow sectors, according to the embodiments herein.

Array 200 shown in FIG. 2 illustrates another example of the embodiments herein, wherein array 200 comprises any of radial-flow assay, a radial-flow assay array, a sector-flow assay, and a sector-flow assay array where one or more test sample fluids are constrained to flow through at least one radial channel or at least one sector channel within one or more substrates including wick (hydrophilic) substrates such as thin layer chromatography substrates, cloth, paper, glass fibers, and polymers, for example, to bind with one or more chemical capture reagents applied to one or more test zones. Specifically, array 200 comprises a circular membrane 210 with at least one predefined sector-flow channel 220 containing at least one chemical capture reagent zone 230, or at least one predefined radial-flow channel 240 containing at least one chemical capture reagent zone 250, at least one centrally disposed test sample fluid input port application pad 260 concentrically surrounded by at least one marker pad 270, at least one fluid flow manifold 280, and at least one wicking pad 290.

The embodiments herein facilitate the inclusion of sensor-imbedded barcodes within the assay or assay array 1, 200 as described in U.S. Patent Publication No. 2009/0020609. Imbedding the sensors or sensor array within a barcode on each assay or assay array requires careful application of the sensor regions to comport with one-, two-, and three-dimensional barcode symbologies to ensure that features of the barcode's encoding symbology remain intact throughout, and after the analyte assay is conducted. Furthermore, the precise, controlled and rapid delivery of the sample analytes to each sensor zones or array of sensor zones is specifically facilitated by the embodiments herein.

Figure 3:
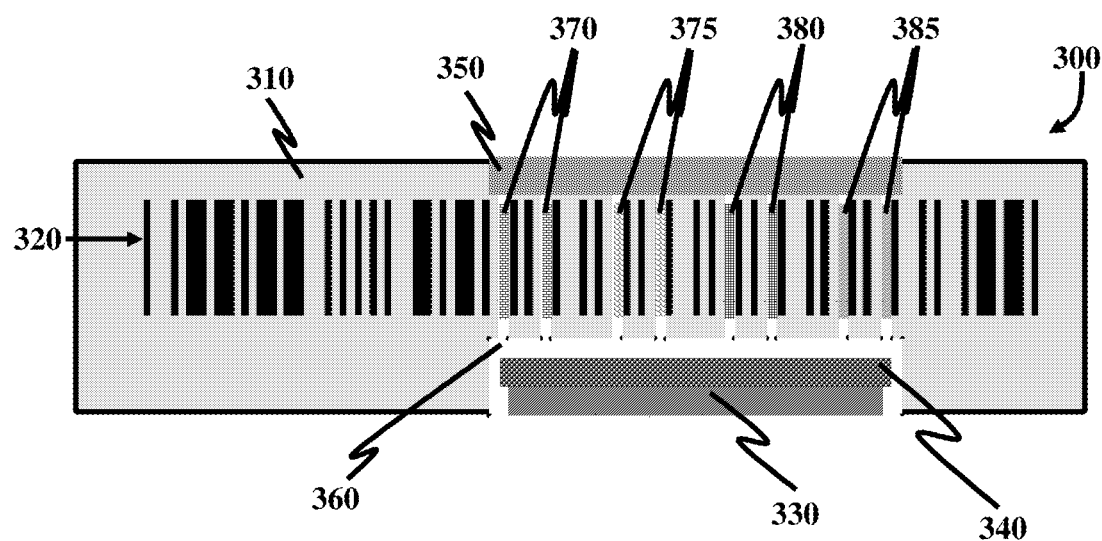
FIG. 3 illustrates a cross-flow, multiplexed analyte assay array imbedded within a machine readable linear barcode, according to the embodiments herein.

FIG. 3 depicts an another embodiment herein, which shows a multiplexed, cross-flow, barcode-imbedded analyte assay array 300 comprising a membrane 310 imbedded within a linear barcode 320, a test sample fluid input port application pad 330, a marker pad 340, a wicking pad 350, and a engineered sample fluid flow manifold 360 contiguous with multiple engineered fluid flow channels wherein one or more chemical capture reagent zones 370, 375, 380, and 385 may be applied. The embodiments herein allow for the ability to simultaneously conduct analyte assays on multiple, independent test sample fluids and to utilize multiple chemical capture reagent compounds to simultaneously conduct multiple, independent analyte assays 300.

Figure 4A:
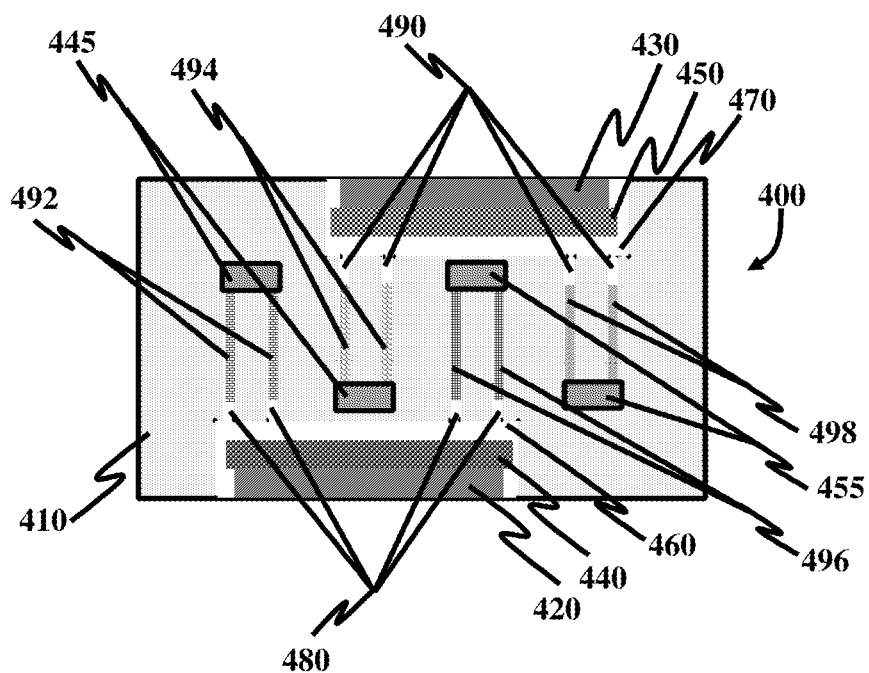
FIG. 4A illustrates a multiple test sample fluid, multiplexed, cross-flow analyte assay array, according to the embodiments herein.
Figure 4B:
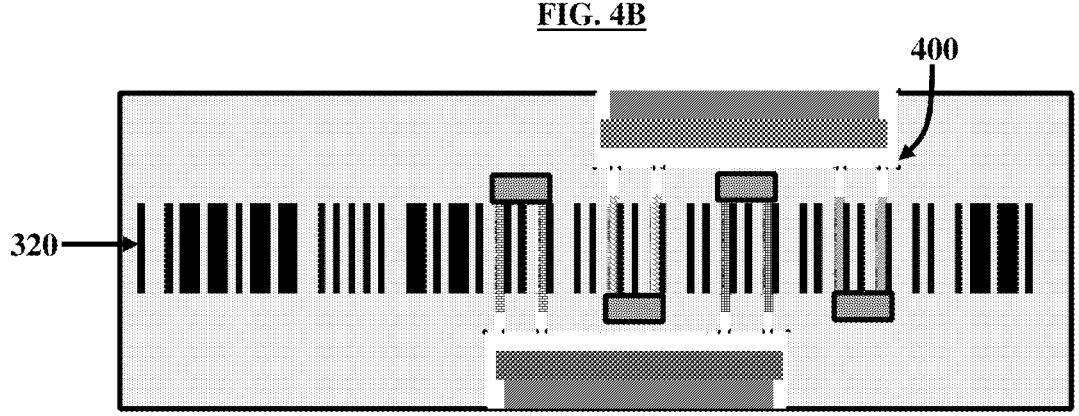
FIG. 4B illustrates the same multiple test sample fluid, multiplexed, cross-flow analyte assay array as depicted in FIG. 4A, imbedded within a linear machine readable barcode, according to the embodiments herein.

FIG. 4A depicts another embodiment herein and specifically provides a multiple test sample fluid, multiplexed, cross-flow analyte assay array 400 comprising a membrane 410, and further includes two independent test sample fluid input port application pads 420 and 430, each contiguous with their respective marker pads 440 and 450, a pair of fluid channel manifolds 460 and 470, a pair of engineered assay channels 480 and 490, and a pair of sample fluid wicking pads 445 and 455. Engineered test sample fluid flow channels 480 contain one or more of the same, or different, chemical capture reagent zones 492 and 496, and independent engineered test sample fluid flow channels 490 contain one or more of the same or different chemical capture reagent zones 494 and 498. FIG. 4B illustrates another embodiment providing the multiple sample, multiplexed cross-flow, analyte assay array 400 of FIG. 4A imbedded within a machine-readable, linear barcode 320.

Alternatively, multi-layered analyte assays or assay arrays can be constructed by overlaying membranes containing one or more flow channels to create a three-dimensional analyte assay or assay array structure. One or more samples can be applied to the multi-layered assay or assay array through one or more sample application input ports, and distributed through fluid flow manifolds to specific flow channels on each chosen membrane layer.

Figure 5:
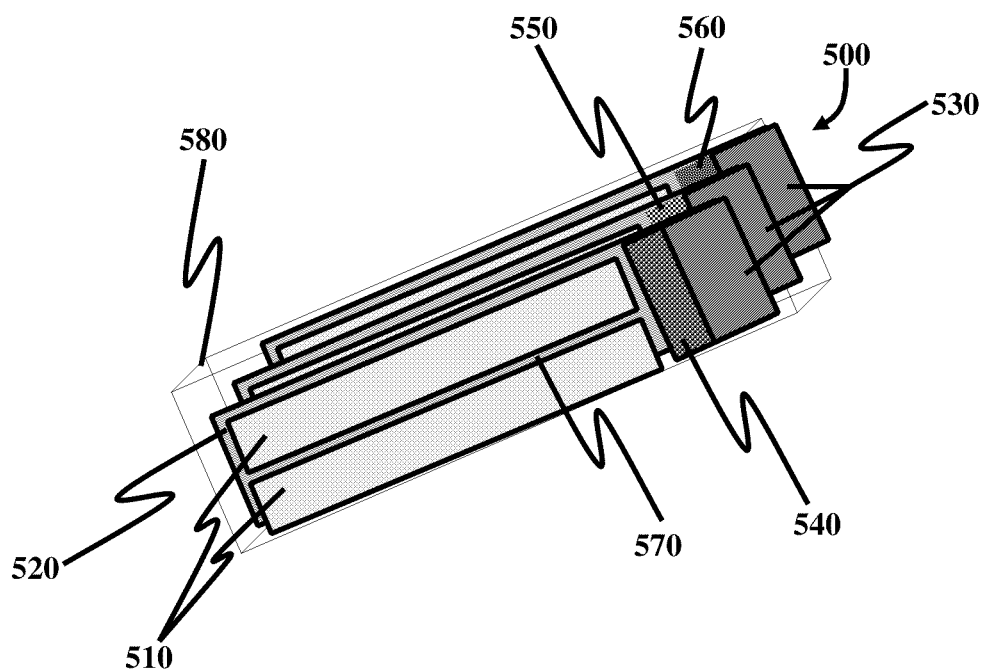
FIG. 5 illustrates a three-dimensional multiplexed analyte assay array structure, according to the embodiments herein.

FIG. 5 depicts one possible embodiment of a three-dimensional assay array structure 500. Specifically test sample fluids are applied at input port application pads 530 contacting marker pads 540, 550, and 560, contiguous with fluid sample flow manifold 570 and chemical capture reagent zones 510, wherein each layer of a three-dimensional analyte assay array is resident on a membrane layer 520. The stacked membrane can be encased in a three-dimensional diagnostic test device 580.

The embodiments herein provide one or more analyte assays or assay arrays which are comprised of one or more engineered channels to direct the flow of, or multiplex, one or more analytes to specific test zones. These fluid flow channels facilitate the controlled flow of one or more analytes in any chosen direction either within a single membrane or multiple membranes, or three-dimensional membrane assemblies. Delivery of test sample analytes only to specific regions within the membrane overcomes limitations of conventional solutions because (i) the volume of a sample analyte is conserved, (ii) the speed of delivery of a sample analyte to a test zone is increased, (iii) the quantity of deposited chemical capture reagents necessary to achieve a desired sensitivity is reduced, and (iv) both qualitative and quantitative analyte assays can be engineered.

Contrary to conventional lateral flow assays where the flow of the test sample analyte is along the longitudinal axis of the membrane, in the embodiments herein, flow channels created within one or more membranes facilitate the flow of one or more analyte test samples along any prescribed direction. The analyte assays or analyte assay arrays may use lateral flow assay markers including but not limited to, charcoal, colloidal gold, latex dyed beads, particles with paramagnetic, magnetic, luminescent, fluorescent or phosphorescent attributes, radioactive particles, and other particles having unique physical, chemical, biological, or radiological properties.

The structure of an assay or assay array's membrane substrate is designed, laid out, printed, grown, deposited, filled, fabricated, patterned, lithographed or etched, so as to create and define one or more preferential fluid flow channels with prescribed dimensions of length, width, height, shape and depth for precise, controlled flow of test sample fluid analytes to predetermined test zones. Test zones can be made for targeting analytes including, but not limited to, proteins, antigens, antibodies, enzymes, nucleic acids and other bio markers. Test sample fluids can be applied through one or more test sample fluid application input ports each comprising at least one sample application pad and at least one assay marker pad. The port feeds a fluid flow manifold that guides or multiplexes a test sample fluid to flow through engineered planar or three-dimensional flow channels.

The embodiments herein extend previous barcode diagnostics work by engineering a new class of diagnostics membrane flow devices that enable testing for multiple targets, including but not limited to, proteins and enzymes, antigens and antibodies and other biological markers, and indicators simultaneously on a single barcode strip analyte assay, and convey (via transmission devices) and store (via storage devices) multiple test data and results autonomously to authorized databases and web portals.

The foregoing description of the specific embodiments will so fully reveal the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments herein have been described in terms of preferred embodiments, those skilled in the art will recognize that the embodiments herein can be practiced with modification within the spirit and scope of the appended claims.

What is claimed is:

1. A lateral flow and flow thru assay device comprising:
    a) at least two membrane analyte assay substrates positioned in parallel rows in different planes;
    b) a plurality of fluid flow channels within each of said two membrane analyte assay substrates;
    c) at least one lateral flow and flow thru assay embedded in each of said fluid flow channels;
    d) at least one test sample pad on each of said membrane analyte assay substrate, said at least one test sample pad receiving and transferring said at least one test sample fluid to said plurality of flow channels and at least one lateral flow assay and flow thru assay on each of said membrane analyte assay substrates;
    (e) at least one contiguous fluid flow manifold within said at least one membrane analyte assay substrate to distribute said at least one test sample, from said test sample application pad to said plurality of lateral flow and flow thru assays;
    f) a marker pad positioned next to and distally to each of said sample pads but before said at least one lateral flow assay of each of said membrane platforms, said marker pad allowing for labeling of analytes of said sample;
    g) at least one analyte assay test zone disposed on each of said lateral flow and flow thru assay: each of said analyte assay test zones being positioned downstream from said marker pad, wherein each of said analyte assay test zones are positioned on a different in-line horizontal location from any other said analyte test zones of said lateral flow assays of said at least two membrane analyte assay substrates;

h) at least one capture reagent disposed at each of the analyte test zones wherein multiple analyte assay test results are simultaneously obtained and in parallel in said diagnostic test device, wherein said lateral flow and flow thru assays on said membrane analyte assay substrates and said analyte assay test zone are positioned to form a readable barcode, and wherein said dispersal of said capture reagent being dispersed in varying band widths to intensity of the color as calibrated by known reagents to allow for a quantitative measurement of the analytes being tested.

2. The lateral flow and flow thru assay device of claim 1, wherein analyte assays are simultaneously conducted on multiple, independent test sample fluids.

3. The lateral flow and flow thru assay device of claim 1, wherein multiple chemical capture reagent compounds are used simultaneously to conduct multiple, distinct, independent analyte assays.

4. The lateral flow and flow thru assay device of claim 1, further comprising at least one quality control zone operatively connected to said at least one analyte assay test zone, wherein at least one chemical capturing control reagent is applied in said at least one analyte assay test zone.

5. The lateral flow and flow thru assay device of claim 1, further comprising at least one sensor imbedded into said at least one contiguous fluid flow channel, wherein an alteration of a state of said at least one sensor indicates information regarding environmental factors affecting a validity of said diagnostic test device.

6. The lateral flow and flow thru assay device of claim 1, wherein at least one different chemical capture reagent is applied in said at least one analyte assay test zone, and wherein a presence of targeted analytes is indicated, and quantitatively measurable in said at least one analyte assay test zone.

7. The lateral flow and flow thru assay device of claim 1, wherein said at least one chemical capture reagent is applied in different titrations in said at least one analyte assay test zone, and wherein a presence of targeted analytes is indicated, and is quantitatively measurable in said at least one analyte assay test zone by means of a bar code reader.

8. The lateral flow and flow thru assay device of claim 1, wherein said any of said multiplexed assay and said multiplexed assay array is imbedded within machine-readable codes comprising a barcode, wherein said machine-readable codes comprise: a) test data; b) test validity; c) test type; and d) test parameters, and wherein said multiple analyte assay test results are indicated by alterations of at least one code within said machine-readable codes.

9. The lateral flow and flow thru assay device of claim 1, wherein said at least one contiguous fluid flow manifold and said at least one contiguous fluid flow channel are formed by the method selected from the group consisting of masking, writing, filling, imbedding, printing, etching, lithography, striping, mechanically forming, laser forming, electron beam forming, ion beam forming, stencil forming, thermoforming, molding, and extruding.

10. The lateral flow and flow thru assay device of claim 1, wherein said at least one contiguous fluid flow channel conserves test sample fluid volume.

11. The lateral flow and flow thru assay device of claim 1, wherein said at least one membrane analyte assay substrates further comprises;

a) a hydrophilic membrane platform; b) a hydrophobic membrane platform; wherein two said hydrophilic membranes platform are separated by at least one said hydrophobic membrane platform.

12. The lateral flow and flow thru assay device of claim 1, wherein said at least one membrane analyte assay substrates comprises a hydrophilic membrane platform sandwiched between two hydrophobic membrane platforms.

13. The lateral flow and flow thru assay device of claim 12, wherein said hydrophilic membrane platform and said hydrophobic membrane platform are interleaved, wherein a plurality of the interleaved platforms are repeatedly stacked to create a three-dimensional multiplexed analyte assay array structure.

14. The lateral flow and flow thru assay device of claim 1, further comprising a barcode comprising machine-readable codes, said codes comprising said multiplexed analyte assay array imbedded therein, wherein said machine-readable codes comprise:

a) test sample fluid identifying information;
b) test data;
c) test validity;
d) test type; and
e) test parameters, wherein said multiple analyte assay test results are indicated by alterations of at least one code within said machine-readable codes.

15. The lateral flow and flow thru assay device of claim 1, further comprising: a barcode structure comprising machine-readable codes comprising said any of at least one multiplexed analyte assay and at least one multiplexed analyte assay array imbedded therein, wherein said machine-readable codes comprise: first data regarding said diagnostic test device comprising any of pre-testing data, test types, lot number, identification number, date of manufacture, date of expiration, environmental factors affecting validity of said multiple analyte assay test results, bounds on operational parameters of said diagnostic test device; and second data regarding said analyte assay test results and validity information of said diagnostic test device after said diagnostic test device has been used; and means for transmitting said first data and said second data to authorized databases and web portals.

16. The lateral flow and flow thru assay device of claim 1, further comprising a case in which to support the membrane analyte assay substrates in parallel position to each other.

\* \* \* \* \*